US00PP15913P2

(12) United States Plant Patent
Hooijman

(10) Patent No.: US PP15,913 P2
(45) Date of Patent: Aug. 9, 2005

(54) ***SOLIDAGO* PLANT NAMED 'PLUTON'**

(50) Latin Name: *Solidago hybrida*
Varietal Denomination: Pluton

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 23 days.

(21) Appl. No.: 10/920,830

(22) Filed: Aug. 18, 2004

(51) Int. Cl.[7] ..... A01H 5/00
(52) U.S. Cl. ..... Plt./263
(58) Field of Search ..... Plt./263

(56) References Cited

U.S. PATENT DOCUMENTS

PP8,710 P * 5/1994 Bartels et al. ..... Plt./263
2002/0138886 P1 * 9/2002 Danziger ..... Plt./263

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of cut flower *Solidago* plant named 'Pluton', characterized by its strong and erect flowering stems; symmetrical branching habit; durable foliage that resists "yellowing"; uniform and freely flowering habit; daisy-type inflorescences with bright yellow-colored ray florets; and good postproduction longevity.

1 Drawing Sheet

Botanical designation: *Solidago hybrida.*
Variety denomination: 'Pluton'.

BACKGROUND OF THE INVENTION

The present Invention relates to a new and distinct cultivar of cut flower *Solidago* plant, botanically known as *Solidago hybrida* and hereinafter referred to by the name 'Pluton'.

The new *Solidago* is a product of a planned breeding program conducted by the Inventor in El Quinche, Pichincha, Ecuador. The objective of the breeding program is to create new cut flower *Solidago* cultivars with durable leaves, strong stems, desirable floret colors and good postproduction longevity.

The new *Solidago* originated from a cross-pollination made by the Inventor in El Quinche, Pichincha, Ecuador in February, 2000, of a proprietary *Solidago* selection identified as Line 52, not patented, as the female, or seed, parent with an unknown *Solidago* selection, not patented, as the male, or pollen, parent. The new *Solidago* was discovered and selected by the Inventor as a single flowering plant within the progeny of the stated cross-pollination grown in a controlled environment in El Quinche, Pichincha, Ecuador. The selection of this plant was based on its durable foliage, strong stems and desirable inflorescence form and attractive ray floret color.

Asexual reproduction of the new *Solidago* by vegetative tip cuttings was first conducted in El Quinche, Pichincha, Ecuador in January, 2001. Asexual reproduction by cuttings has shown that the unique features of this new *Solidago* are stable and reproduced true to type in successive generations.

SUMMARY OF THE INVENTION

The cultivar Pluton has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Pluton'. These characteristics in combination distinguish 'Pluton' as a new and distinct cut flower *Solidago:*

1. Strong and erect flowering stems.
2. Symmetrical branching habit.
3. Strong foliage that resists "yellowing".
4. Uniform and freely flowering habit.
5. Daisy-type inflorescences with bright yellow-colored ray florets.
6. Good postproduction longevity.

Plants of the new *Solidago* can be compared to plants of the female parent selection. Plants of the new *Solidago* differ from plants of the female parent selection primarily in foliage durability as plants of the new *Solidago* have more durable foliage than plants of the female parent selection.

Plants of the new *Solidago* can be compared to plants of the cultivar Tara, not patented. In side-by-side comparisons conducted in El Quinche, Pichincha, Ecuador plants of the new *Solidago* differed from plants of the cultivar Tara in the following characteristics:

1. Plants of the new *Solidago* were taller and broader than plants of the cultivar Tara.
2. Plants of the new *Solidago* had longer lateral stems with longer internodes than plants of the cultivar Tara.
3. Foliage of plants of the new *Solidago* was more durable than foliage of plants of the cultivar Tara.
4. Plants of the new *Solidago* had longer leaves than plants of the cultivar Tara.

BRIEF DESCRIPTION OF THE PHOTOGRAPHS

The accompanying colored photographs illustrate the overall appearance of the new *Solidago* showing the colors as true as it is reasonably possible to obtain in colored reproductions of this type. Colors in the photographs may differ from the color values cited in the detailed botanical description which accurately describe the colors of the new *Solidago*.

The photograph at the top of the sheet comprises a side perspective view of a typical flowering plant of 'Pluton'.

The photograph at the bottom of the sheet is a close-up view of a typical flowering stem of 'Pluton'.

DETAILED BOTANICAL DESCRIPTION

In the following description, color references are made to The Royal Horticultural Society Colour Chart, 2001 Edition, except where general terms of ordinary dictionary significance are used. The aforementioned photographs, following observations and measurements describe plants grown and flowered during the fall and winter in El Quinche, Pichincha, Ecuador, in an outdoor nursery and under conditions which approximate those generally used in commercial cut flower *Solidago* production. During the production of these plants, day temperatures ranged from 12 to 30° C. and night temperatures ranged from 5 to 12° C. Plants were about eight to nine months from planting rooted young plants when the photographs and the botanical description were taken.

Botanical classification: *Solidago hybrida* cultivar Pluton.

Parentage:

*Female, or seed, parent.*—Proprietary *Solidago hybrida* selection identified as Line 52, not patented.

*Male, or pollen, parent.*—Unknown *Solidago hybrida* selection, not patented.

Propagation:

*Type.*—Terminal vegetative cuttings.

*Time to initiate roots.*—About 12 to 16 days at 17 to 25° C.

*Time to produce a rooted young plant.*—About 30 to 35 days at 17 to 25° C.

*Root description.*—Fine, fibrous; 162D to 161D in color.

*Rooting habit.*—Freely branching.

Plant description:

*Appearance.*—Herbaceous daisy-type cut flower *Solidago*. Flowering stems upright and strong. Vigorous. Symmetrical branching habit with long lateral branches.

*Plant height.*—About 109 cm.

*Plant width.*—About 27 cm.

*Lateral branches.*—Quantity per plant: About 20. Length: About 29 cm. Diameter: About 1.7 mm. Internode length: About 2.7 cm. Strength: Strong. Texture: Pubescent. Color: 144A to 137C.

*Foliage description.*—Arrangement: Alternate, simple. Durability: Leaves durable resisting "yellowing". Length: About 14.9 cm. Width: About 2 cm. Shape: Lanceolate. Apex: Acute. Base: Attenuate. Margin: Sparsely serrate. Texture, upper and lower surfaces: Pubescent; rough. Color: Developing foliage, upper surface: 137B. Developing foliage, lower surface: 137C to 146B. Fully expanded foliage, upper surface: 137A; venation, 146C to 144A. Fully expanded foliage, lower surface: 137C to 138A; venation, 146A to 137B. Petiole length: About 3.5 mm. Petiole diameter: About 2.5 mm. Petiole color, upper surface: 146C to 144A. Petiole color, lower surface: 146A to 137B.

Inflorescence description:

*Appearance.*—Daisy-type inflorescence form with narrowly elliptic-shaped ray florets. Inflorescences terminal or axillary. Disc and ray florets develop acropetally on a capitulum. Inflorescences not fragrant. Inflorescences persistent. Inflorescences face upright to outwardly. Uniform and freely flowering habit.

*Flowering response.*—Plants flower year-round in Ecuador. Plants begin flowering about 18 weeks after planting.

*Postproduction longevity.*—Inflorescences maintain good color and substance for about two weeks as a cut flower.

*Quantity of inflorescences.*—About 342 inflorescences develop per lateral branch.

*Inflorescence bud.*—Height: About 3.6 mm. Diameter: About 2 mm. Shape: Nearly oval. Color: 144C to 145B.

*Inflorescence size.*—Diameter: About 4.6 mm. Depth (height): About 3.9 mm. Diameter of disc: About 1.75 mm. Receptacle height: About 2.1 mm. Receptacle diameter: About 3.1 mm.

*Ray florets.*—Number of ray florets per inflorescence/arrangement: About 15 arranged in a single whorl. Length: About 3.4 mm. Width: About 0.8 mm. Shape: Narrowly elliptic. Apex: Obtuse with emarginations. Base: Attenuate. Margin: Entire. Texture, upper and lower surfaces: Smooth, glabrous. Orientation: Initially upright, then mostly incurved. Color: When opening, upper surface: 3A. When opening, lower surface: 2A. Fully opened, upper surface: 9A. Fully opened, lower surface: 2A.

*Disc florets.*—Arrangement: Massed at center of receptacle. Number of disc florets per inflorescence: About seven. Length: About 5.3 mm. Diameter, apex: About 2.5 mm. Diameter, base: About 0.5 mm. Shape: Tubular, salverform, elongated. Apex: Five lobes; lobes acute. Color, immature: 7A. Color, mature: Apex and mid-section: 5A. Base: 145C.

*Phyllaries.*—Quantity per inflorescence: About 19. Length: About 2.2 mm. Width: About 0.6 mm. Shape: Narrowly deltoid. Apex: Acute. Base: Truncate. Texture, upper and lower surfaces: Smooth, glabrous. Color, upper surface: 151B to 150A. Color, lower surface: N144C to 150C.

*Peduncles.*—Length, terminal peduncle: About 4.3 mm. Length, fourth peduncle: About 3.6 mm. Length, seventh peduncle: About 5.1 mm. Diameter: About 0.4 mm. Aspect: Erect to about 18° from vertical. Strength: Strong. Texture: Pubescent. Color: N144C.

*Reproductive organs.*—Androecium: Present on disc florets only. Quantity per disc floret: One. Anther shape: Linear. Anther length: About 0.9 mm. Anther color: 13A. Pollen amount: Scarce. Pollen color: 13A. Gynoecium: Present on both ray and disc florets. Quantity per floret: One. Pistil length: About 5.3 mm. Stigma shape: Bilobed; lobes linear. Stigma color: 5B. Style length: About 3.6 mm. Style color: 1C. Ovary color: 1D.

*Seed.*—Length: With pappus, about 2.5 mm; without pappus, about 2 mm. Diameter: About 1 mm. Color: Dried, 199A to N199B.

Disease/pest resistance: Resistance to pathogens and pests common to *Solidagos* has not been observed on plants grown under commercial greenhouse conditions.

Temperature tolerance: Plants of the new *Solidago* have been observed to tolerate temperatures from about 7 to about 30° C.

It is claimed:

1. A new and distinct cultivar of cut flower *Solidago* plant named 'Pluton', as illustrated and described.

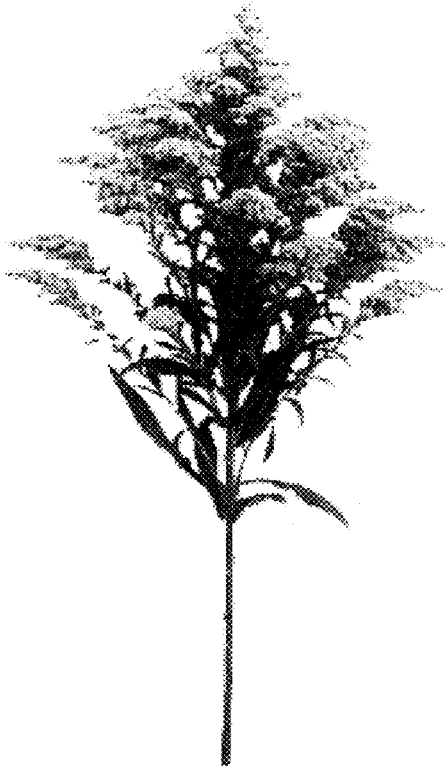
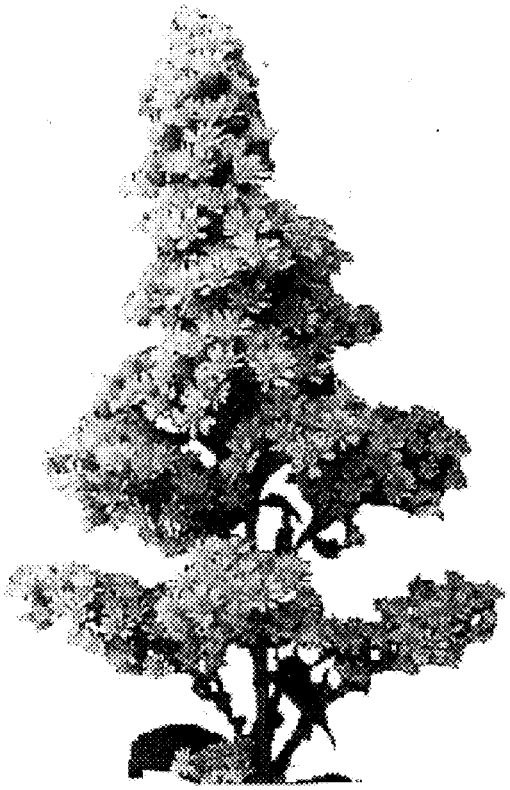

* * * * *